(12) United States Patent
Schena et al.

(10) Patent No.: US 8,342,054 B2
(45) Date of Patent: Jan. 1, 2013

(54) MULTIAXIS COUNTERBALANCE AND POSITIONING SYSTEM USING A SPATIAL LINKAGE

(75) Inventors: Bruce Michael Schena, Menlo Park, CA (US); Roman L. Devengenzo, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 311 days.

(21) Appl. No.: 12/693,329

(22) Filed: Jan. 25, 2010

(65) Prior Publication Data

US 2010/0116082 A1 May 13, 2010

Related U.S. Application Data

(62) Division of application No. 11/864,702, filed on Sep. 28, 2007, now Pat. No. 7,677,129.

(51) Int. Cl.
*B25J 18/00* (2006.01)
(52) U.S. Cl. .................. 74/490.05; 74/490.01; 901/28; 901/48
(58) Field of Classification Search .............. 74/490.01, 74/490.05, 490.06; 414/719, 917; 901/15–17, 901/41, 48
See application file for complete search history.

(56) References Cited

U.S. PATENT DOCUMENTS

| | | | |
|---|---|---|---|
| 3,419,238 A | 12/1968 | Flory | |
| 3,721,416 A | 3/1973 | Goudreau | |
| 4,659,278 A | 4/1987 | Doege et al. | |
| 4,666,364 A * | 5/1987 | Doege et al. | 414/742 |
| 4,739,241 A | 4/1988 | Vachtsevanos et al. | |
| 5,740,699 A | 4/1998 | Ballantyne et al. | |
| 5,817,084 A * | 10/1998 | Jensen | 606/1 |
| 6,210,097 B1 * | 4/2001 | Kim et al. | 414/522 |
| 2004/0024385 A1 * | 2/2004 | Stuart | 606/1 |
| 2004/0097966 A1 | 5/2004 | Nakamura | |
| 2004/0111113 A1 | 6/2004 | Nakamura et al. | |
| 2005/0072261 A1 | 4/2005 | Okada et al. | |
| 2006/0156850 A1 | 7/2006 | Mueller | |
| 2006/0196299 A1 | 9/2006 | Taboada et al. | |
| 2008/0002881 A1 | 1/2008 | Miyaki | |
| 2008/0028881 A1 * | 2/2008 | Sone et al. | 74/471 R |

FOREIGN PATENT DOCUMENTS

| | | |
|---|---|---|
| EP | 0595291 | 5/1994 |
| WO | 9713997 A1 | 4/1997 |

OTHER PUBLICATIONS

Vertut, Jean and Philippe Coiffet, Teleoperation and Robotics: Evolution and Development, English translation, Prentice-Hall, Inc., Inglewood Cliffs, NJ, USA, 1986.

(Continued)

*Primary Examiner* — Phillip A Johnson

(57) ABSTRACT

A spatial linkage including an inboard gimbal plate that provides a ground for the spatial linkage, an outboard gimbal plate, and at least three links that couple the outboard gimbal plate to the inboard gimbal plate. Each link has a longitudinal axis and two pivotal couplings disposed at opposite ends of the longitudinal axis. Each link is pivotally coupled to the outboard gimbal plate at a first end of the longitudinal axis and pivotally coupled to the inboard gimbal plate at a second end of the longitudinal axis opposite the first end. The pivotal couplings allow the outboard gimbal plate to move relative to the inboard gimbal plate and preventing relative rotation between the outboard gimbal plate and the inboard gimbal plate. Counterweight is coupled to at least one of the links on the opposite side of the inboard gimbal plate from the outboard gimbal plate.

20 Claims, 7 Drawing Sheets

OTHER PUBLICATIONS

PCT/US08/76129 International Search Report, mailed Feb. 12, 2009, 4 pages.

PCT/US0876129 Written Opinion of the International Searching Authority, mailed Feb. 12, 2009, 6 pages.

* cited by examiner

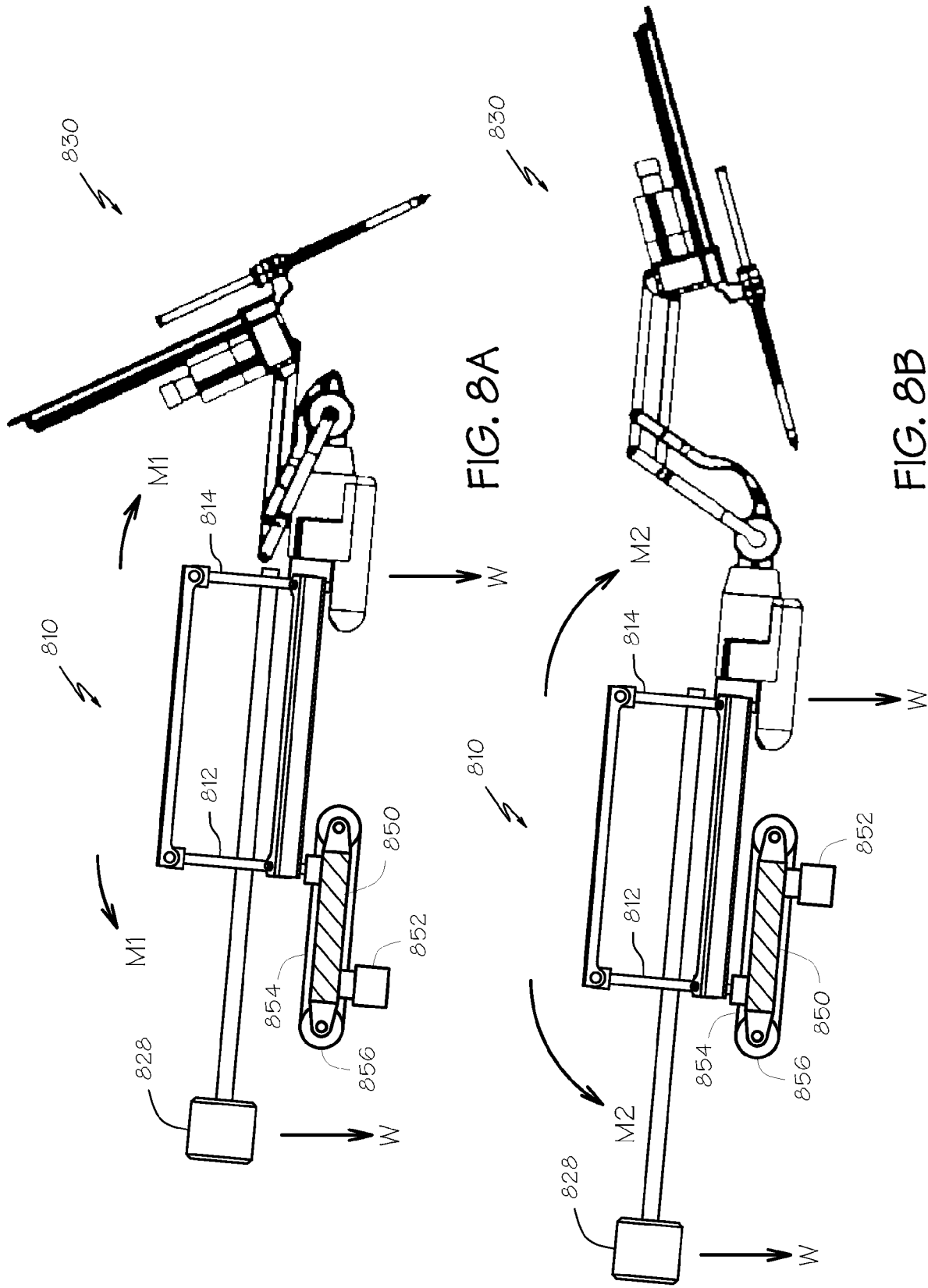

MULTIAXIS COUNTERBALANCE AND POSITIONING SYSTEM USING A SPATIAL LINKAGE

CROSS REFERENCE TO RELATED APPLICATIONS

This application is a divisional of application Ser. No. 11/864,702, filed Sep. 28, 2007, which is hereby incorporated by reference in its entirety.

BACKGROUND

A setup joint system may be used to position a device, such as a robotic arm, in an initial position. Such systems may also be known as pre-positioning systems. A setup joint system should allow the device to be moved freely in space so it can be located as necessary and then rigidly locked in the initial position for use.

Setup joint systems may be used in a robotic surgical system to position robotic surgical arms around a patient prior to surgery. In a robotic surgical system a surgeon manipulates robotic laproscopic surgical instruments robotically from a surgeon's console. The console provides a video screen that shows the instruments being manipulated at the surgical site. The console further provides master arms that the surgeon physically manipulates to operate the robotic laproscopic surgical instruments. It is desired to create the visual illusion that the surgeon is directly manipulating the surgical instruments so that the manipulations are intuitive and the presence of the robotic surgical system becomes transparent.

An important consideration for achieving a transparent and intuitive surgeon's console is providing good angular alignment of the remote robotic "hands" as seen on the viewing screen with the surgeon's real hands located on the master arms. If the setup joint system allows rotation of the supported robotic surgical arms, then position sensors are required to provide the angular orientation of the robotic surgical arms in the initial position in order to provide intuitive control to the surgeon. It is desirable that the setup joint system prevent rotation of the supported robotic surgical arms so that the angular orientation is fixed and the need for angular sensor input is eliminated.

A setup joint system for use in a robotic surgical system should be precisely counterbalanced to allow the operating room staff to easily position the robotic arm without risk of having the arm or setup joints collide with the patient. The system should be compact because space around the patient in an operating room is at a premium. The outboard weight of the system should be low to increase the stiffness and resonant frequency of the system.

It is desirable to mount the setup joint system to the operating table so that the possibility of relative movement between the setup joint system and the patient is reduced. Since the operating table may be tilted to improve patient access, a setup joint system that is mounted to the operating table should be gravity neutral so that it remains substantially balanced as it changes orientation relative to the direction of gravitational forces.

SUMMARY

A spatial linkage including an inboard gimbal plate that provides a ground for the spatial linkage, an outboard gimbal plate, and at least three links that couple the outboard gimbal plate to the inboard gimbal plate. Each link has a longitudinal axis and two pivotal couplings disposed at opposite ends of the longitudinal axis. Each link is pivotally coupled to the outboard gimbal plate at a first end of the longitudinal axis and pivotally coupled to the inboard gimbal plate at a second end of the longitudinal axis opposite the first end. The pivotal couplings allow the outboard gimbal plate to move relative to the inboard gimbal plate and prevent relative rotation between the outboard gimbal plate and the inboard gimbal plate. Counterweight is coupled to at least one of the links on the opposite side of the inboard gimbal plate from the outboard gimbal plate.

Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which:

FIG. 8A is a side elevation of another embodiment of the invention.

FIG. 8B is a side elevation of the embodiment of FIG. 7A in a second operative position.

DETAILED DESCRIPTION

Figure 1:
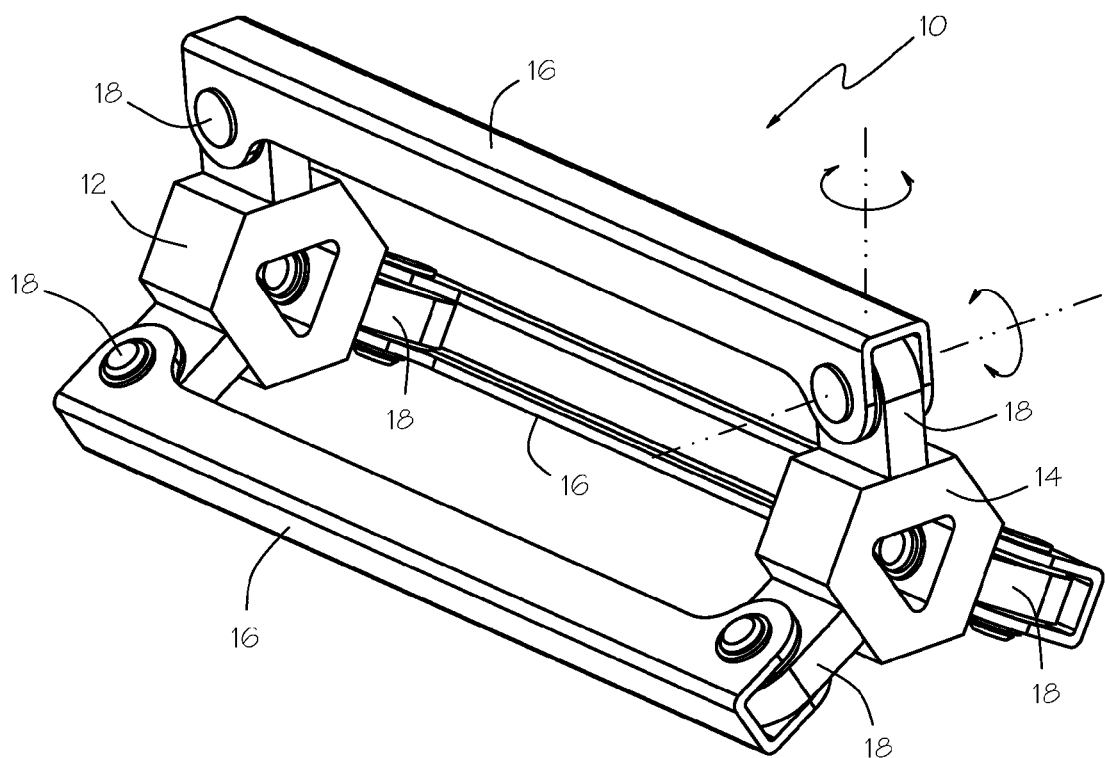
FIG. 1 is a pictorial view of an embodiment of the invention.

FIG. 1 shows a spatial linkage 10 that embodies the invention. An inboard gimbal plate 12 provides a mechanical ground for the spatial linkage 10. Ground is used to mean a frame of reference for the spatial linkage. While the inboard gimbal plate 12 may move relative to other components, it is considered the immovable foundation of the spatial linkage 10.

An outboard gimbal plate 14 is coupled to the inboard gimbal plate 12 by three links 16. In other embodiments there may be additional redundant links that further couple the outboard gimbal plate to the inboard gimbal plate. Each link 16 has a longitudinal axis and two pivotal couplings 18 disposed at opposite ends of the longitudinal axis. Each link 16 is pivotally coupled to the outboard gimbal plate 14 at a first end of the longitudinal axis by one of the pivotal couplings 18 and pivotally coupled to the inboard gimbal plate 12 at a second end of the longitudinal axis opposite the first end by the second pivotal coupling.

As suggested by the axes of rotation shown for the upper right pivotal coupling 18 in FIG. 1, each pivotal coupling allows the link 16 to rotate relative to the coupled gimbal plate 14 with respect to two axes. The link 16 constrains the motion of the outboard gimbal plate 14 relative to the inboard gimbal plate 12 for all other motions. The pivotal coupling 18 illustrated is a clevis pivot. The clevis allows the link 16 to rotate only about the axis of the clevis pin. The clevis is pivotally coupled to the gimbal plate 12, 14 allowing the clevis and the coupled link 16 to rotate about a second axis. Thus the clevis pivot allows the link 16 to rotate relative to the coupled gimbal plate 14 with respect to two axes while constraining the link with respect to all other movement relative to the coupled gimbal plate 14.

Figure 2:
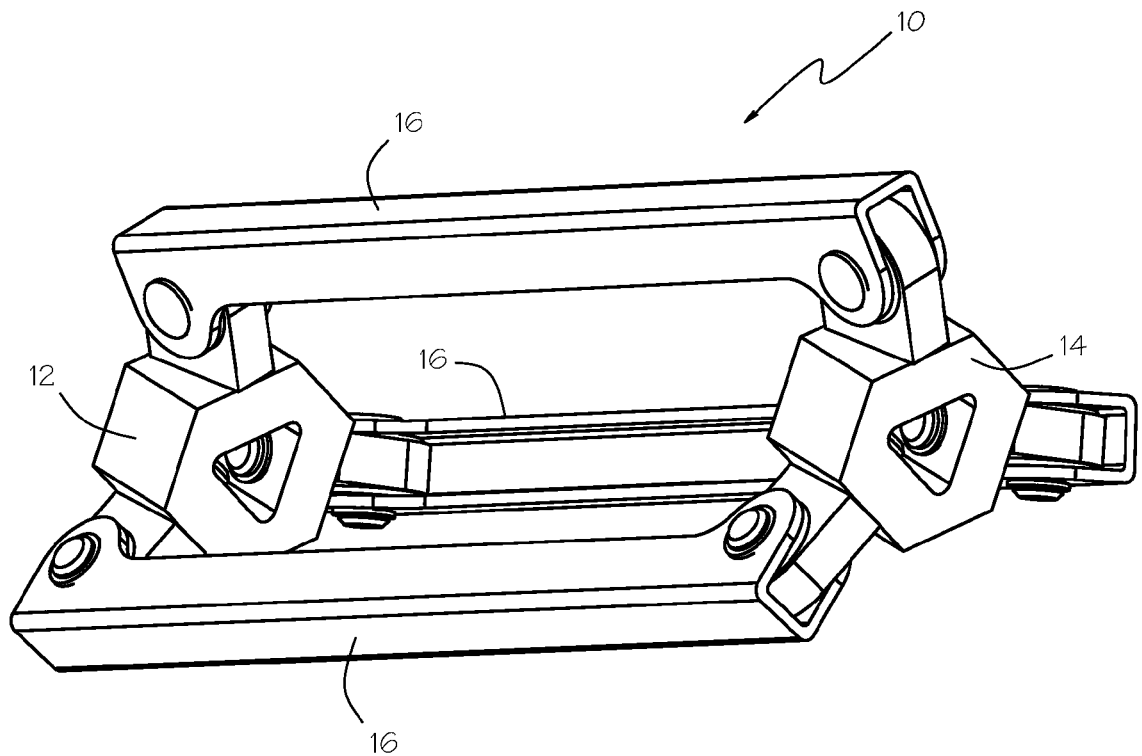
FIG. 2 is a pictorial view of the embodiment of FIG. 1 in a second operative position.

As may be seen in FIG. 2, the pivotal couplings 18 allow the outboard gimbal plate 14 to move relative to the inboard gimbal plate 12 while preventing relative rotation between the outboard gimbal plate and the inboard gimbal plate. As a result, the outboard gimbal plate 14 is always parallel to the inboard gimbal plate 12. Thus a device rigidly supported by the outboard gimbal plate 14 will remain in a fixed angular relationship to the grounded inboard gimbal plate 12. The motion of the supported device will be limited to translation with two degrees of freedom.

Figure 3:
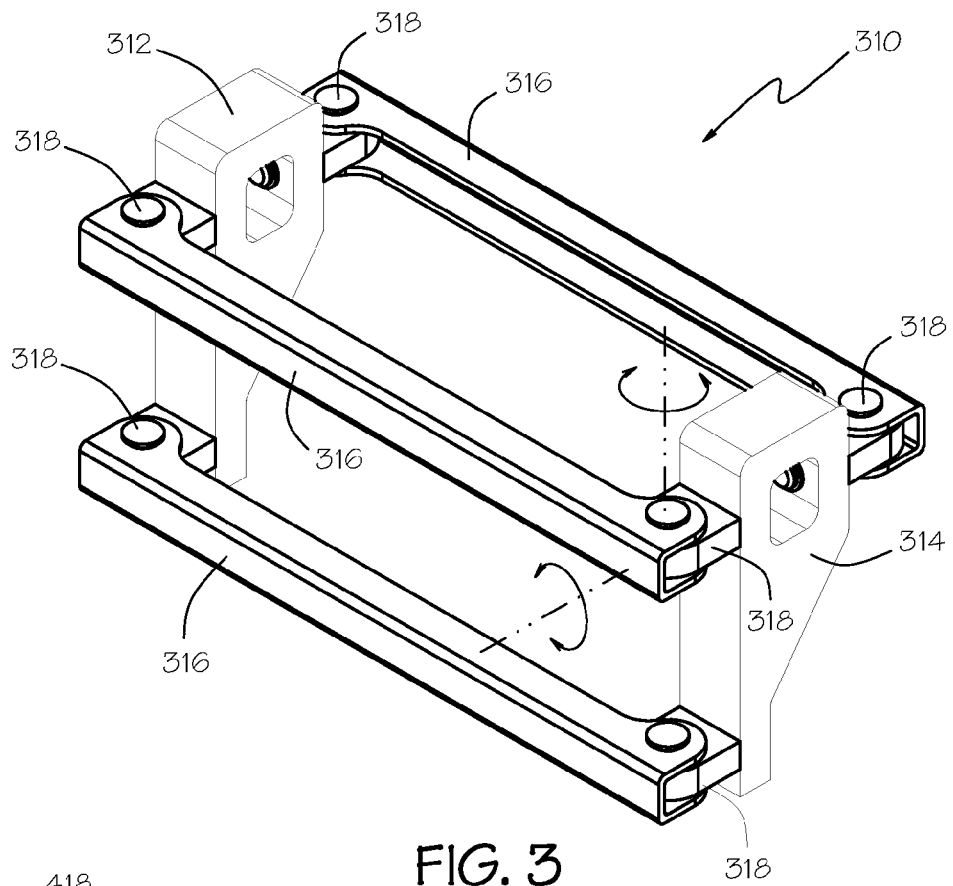
FIG. 3 is a pictorial view of another embodiment of the invention.

FIG. 3 shows another spatial linkage 310 that embodies the invention. As in the preceding embodiment, an outboard gimbal plate 314 is coupled to an inboard gimbal plate 312 by three links 316. It will be seen that the links need not be in a symmetrical arrangement. The pivotal couplings 318 are similar to those of the preceding embodiment.

Figure 4:
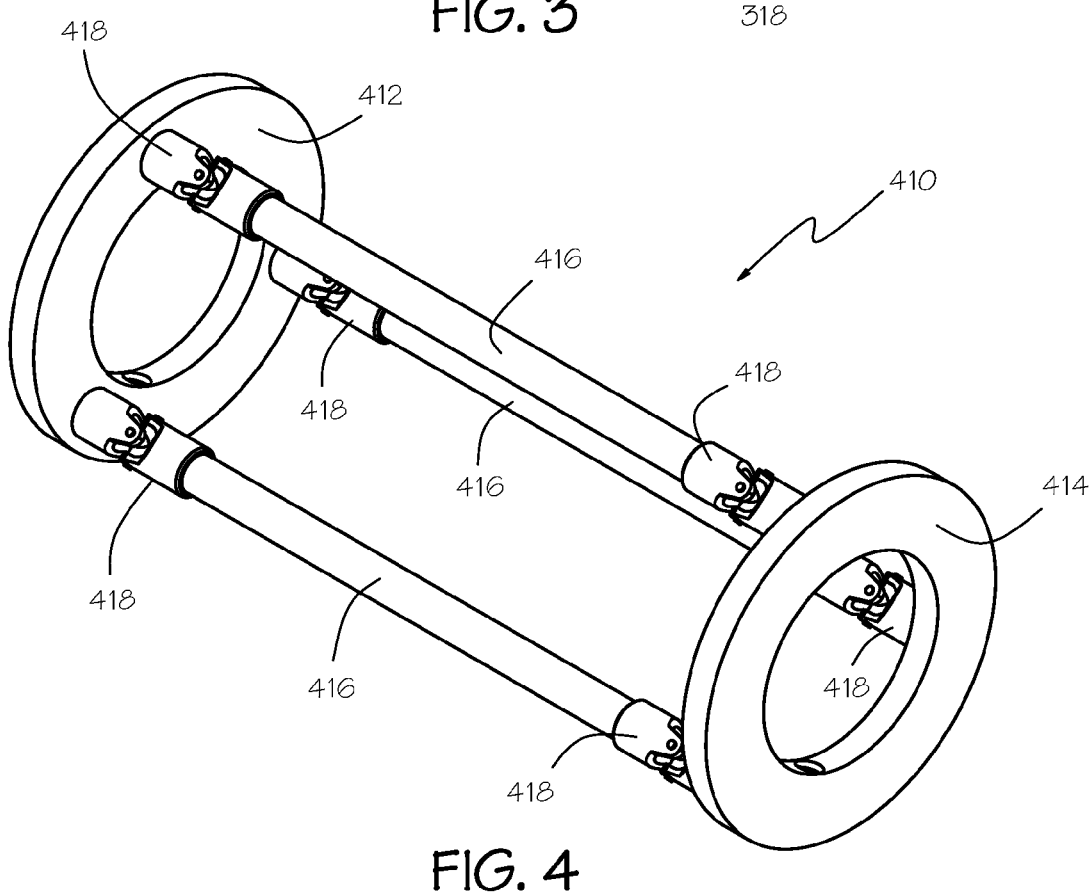
FIG. 4 is a pictorial view of another embodiment of the invention.

FIG. 4 shows another spatial linkage 410 that embodies the invention. As in the preceding embodiments, an outboard gimbal plate 414 is coupled to an inboard gimbal plate 412 by three links 416. In this embodiment the pivotal couplings 418 are in the form of universal joints. The range of motion of universal joints may be less than the pivotal couplings shown in the preceding embodiments.

Figure 5:
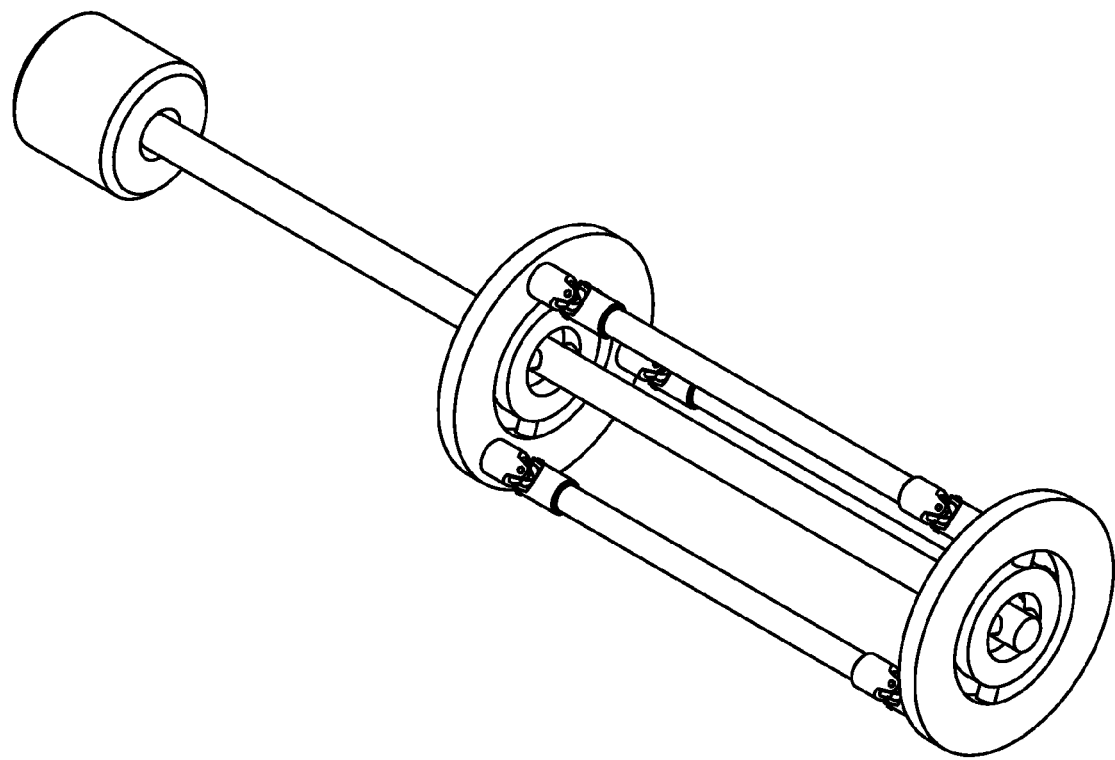
FIG. 5 is a pictorial view of another embodiment of the invention that includes a counterweight.

As shown in FIG. 5, the spatial linkage 510 may be used to provide a counterbalanced support assembly. The spatial linkage 510 may include a counterweight link 520 having a first end 526 and an opposing second end 522 on a longitudinal axis. The counterweight link 520 may be pivotally coupled to the outboard gimbal plate 514 at the first end 526 of the longitudinal axis and pivotally coupled to the inboard gimbal plate 512 at a third point 524 between the first end 526 and the second end 522 on the longitudinal axis. The distance between the first end 526 and the third point 524 on the longitudinal axis of the counterweight link 520 is the same as the distance between the first end 517 and second end 515 of the longitudinal axis for each of the three links 516. The longitudinal axis of the counterweight link 520 is parallel to the longitudinal axes of the three links 516. A counterweight 528 may coupled to the second end 522 of the counterweight link 520 to counterbalance the spatial linkage 510 and a load supported by the outboard gimbal plate 514.

Figure 6:
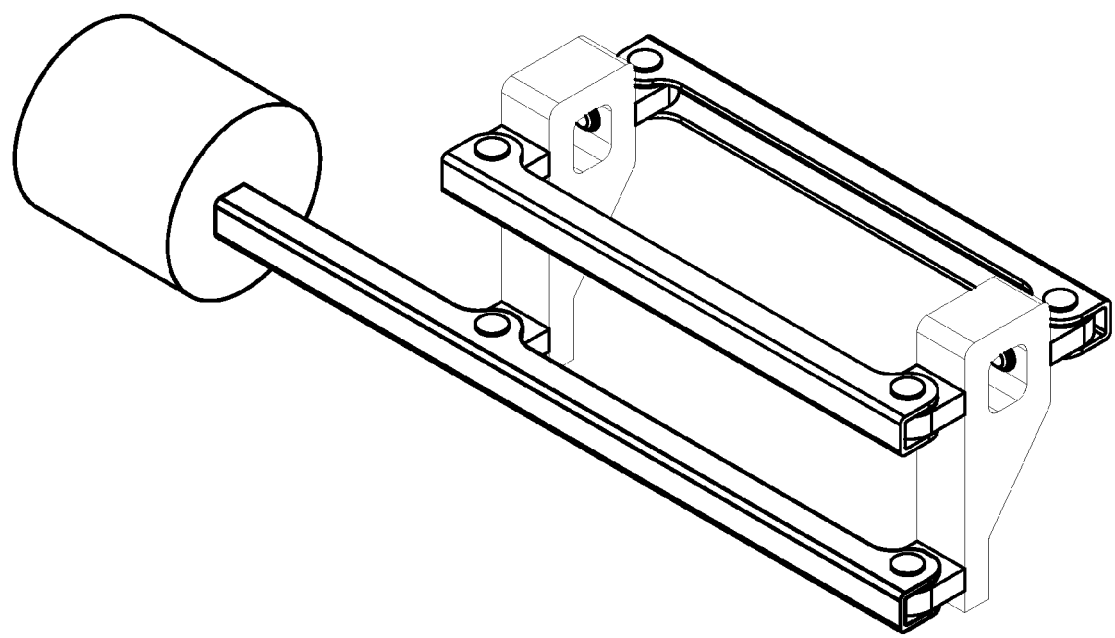
FIG. 6 is a pictorial view of another embodiment of the invention that includes a counterweight.

As shown in FIG. 6, the counterweight link 620 may include one of the three links 616. The third point 624 of the longitudinal axis of the counterweight link 620 is the same as the second end 615 of the longitudinal axis of the included one of the three links 616.

Figure 7A:
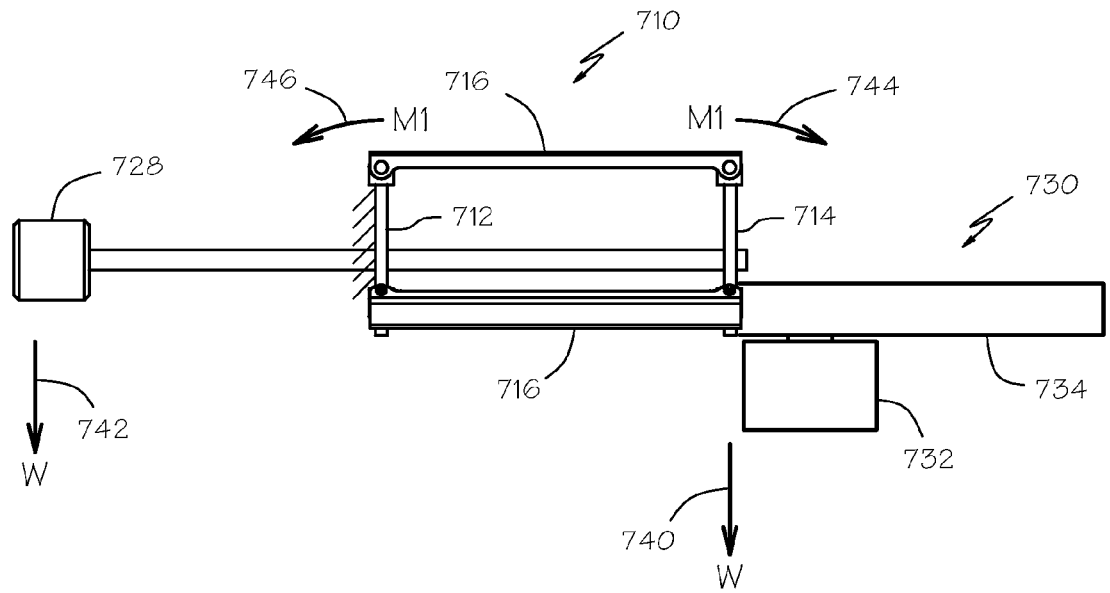
FIG. 7A is a side elevation of another embodiment of the invention.
Figure 7B:
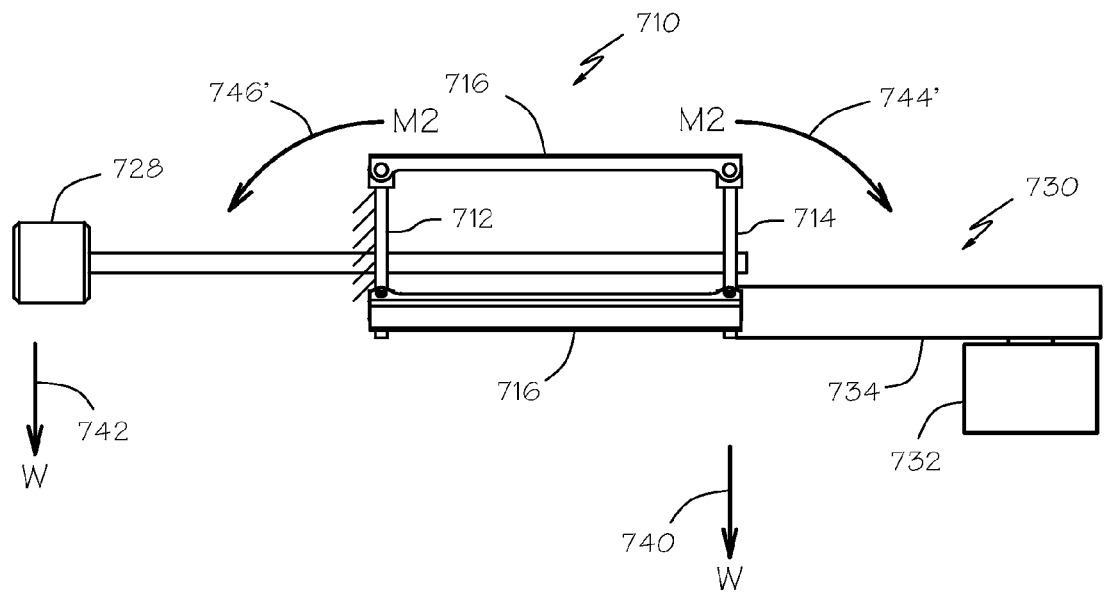
FIG. 7B is a side elevation of the embodiment of FIG. 7A in a second operative position.

As shown in FIGS. 7A and 7B, the spatial linkage 710 may support a cantilevered load 730 rigidly coupled to the outboard gimbal plate 714. The spatial linkage 710 with the coupled cantilevered load 730 may be counterbalanced by a counterweight 728. The cantilevered load 730 may have a movable center of gravity. For example, the cantilevered load 730 may be a load 732 on a linear slide 734 that provides an additional degree of freedom for the load. As the load 732 is moved from a first position shown in FIG. 7A to a second position shown in FIG. 7B the center of gravity of the load moves away from the outboard gimbal plate 714. Perhaps surprisingly, the spatial linkage 710 with the coupled cantilevered load 730 will remain in balance regardless of the movement of the center of gravity of the cantilevered load. It will be appreciated that a load on a linear slide may require a counterbalance with respect to the slide if the slide is not maintained perpendicular to gravity (horizontal).

The cantilevered load 730 is rigidly coupled to and supported by the outboard gimbal plate 714. The outboard gimbal plate supports the weight of the load 730 as indicated by the vector W in the direction of gravity. The weight of the load 730 is counterbalanced by the counterweight 728 as indicated by the second vector W. (The counterweight also counterbalances the weight of spatial linkage 710).

The outboard gimbal plate 714 further supports a rotational force due to the displacement of the center of gravity of the load from the outboard gimbal plate indicated by the vector M1 744. As the center of gravity of the load moves away from the outboard gimbal plate 714, the rotational force on the outboard gimbal plate increases as indicated by the vector M2 744' in FIG. 7B. The three links 716 constrain the outboard gimbal plate 714 to remain parallel to the inboard gimbal plate 712. Therefore the rotational forces on the outboard gimbal plate 714 are transferred to the inboard gimbal plate 712 as indicated by the equal and opposite vector M1 746. The inboard gimbal plate 712 is the grounded member of the spatial linkage 710 and it provides the necessary reaction force to any applied load. Thus, changes in the center of gravity of the load 730 only change the rotational forces on the gimbal plates which are supported to ground. Only the unchanging weight of the load 730 is supported by the counterweight. It will be appreciated that while inboard gimbal plate 712 is the ground member of the spatial linkage 710, it may be movably supported.

As shown in FIGS. 8A and 8B, the inboard gimbal plate 812 of the spatial linkage 810 may supported by a grounded sliding support 850 such that the inboard gimbal plate is movable laterally along the length of the sliding support and is constrained in all other lateral directions and rotations. The load supported by the outboard gimbal plate 814 may be a surgical robotic arm 830. The arrangement illustrated in FIGS. 8A and 8B may be used as a setup joint system for the robotic arm 830. It will be appreciated that the robotic arm 830 could be connected to the outboard gimbal plate 814 with a linear slide similar to that illustrated in FIGS. 7A and 7B to provide an additional degree of freedom.

As the robotic arm extends from a first position shown in FIG. 8A to a second position shown in FIG. 8B, the changing center of gravity of the load creates a changing gravitational moment load on the outboard gimbal plate 814 that is reacted by the grounded inboard gimbal plate 812 as previously described. The load of the surgical robotic arm 830 remains counterbalanced by the counterweight 828 regardless of the movement of the surgical robotic arm or movement of the inboard gimbal plate 812 laterally along the sliding support 850 because the inboard gimbal plate is constrained from rotating. The inboard gimbal plate 812 remains grounded through the grounded sliding support 850 so that it can react the changing moment at the outboard gimbal plate 814 created by the changing center of gravity of the load 830.

If the sliding support 850 is not maintained perpendicular to gravity (horizontal), a counterbalance may be provided as part of the sliding support to maintain the position of the spatial linkage 810 on the sliding support. As shown, the counterbalance may be in the form of a sliding counterweight 852 coupled to the sliding support 850 such that the counterweight is movable laterally along the length of the sliding support. The counterweight 852 is coupled to the inboard gimbal plate 812 such that the counterweight provides a force on the inboard gimbal plate that is equal and opposite to the gravitational force on the inboard gimbal plate. In the example shown in FIGS. 8A and 8B, the counterweight 852 has a mass equal to the mass of all components attached to and including the inboard gimbal plate 812. The counterweight 852 and total outboard mass of components attached to and including the inboard gimbal plate 812 are equally affected by gravity because they are coupled to the sliding support 850 such that they are both inclined equally. A cable 854 and pulley 856 arrangement allows the counterweight 852 to counteract the gravitational forces on the inboard gimbal plate 812. Two pulleys may support the cable in a loop configuration to provide a counterbalance inclining the sliding support in either direction and to maintain cable tension when the sliding support is substantially horizontal.

The gimbal plates and links provide two degrees of freedom for the load supported by the outboard gimbal plate. As discussed above, the inboard may be gimbal plate coupled to ground with a sliding connection to provide a third degree of freedom. In some applications it may be desirable to provide a third degree of freedom without the use of a sliding connection.

Figure 9:
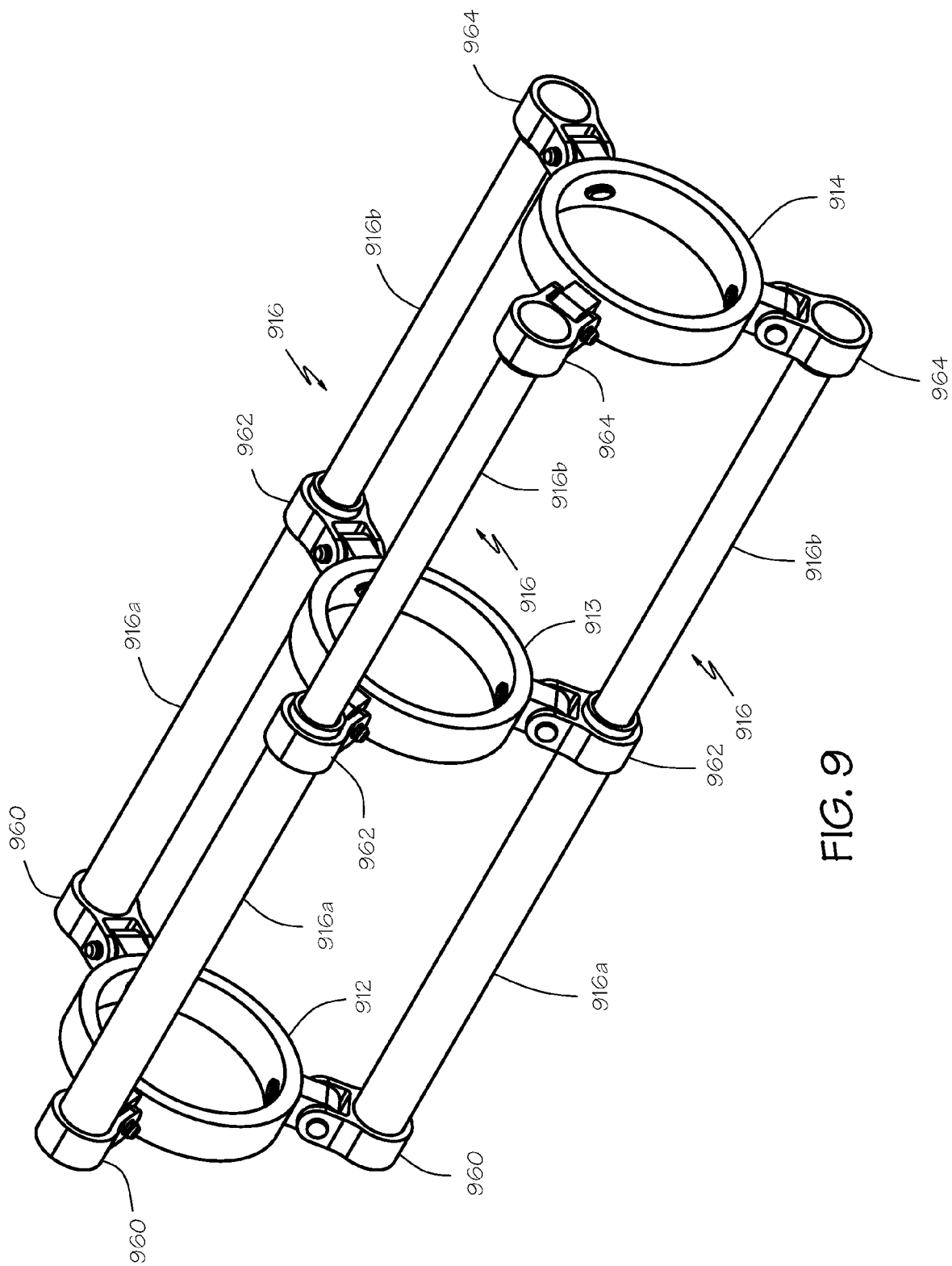
FIG. 9 is a pictorial view of another embodiment of the invention.

FIG. 9 shows an embodiment of the spatial linkage in which a distance between a first end 960 and a second end 964 of the longitudinal axis of each link 916 is adjustable such that the distance remains equal for each of the three links. In the embodiment shown, each link 916 includes an outer portion 916a and an inner portion 916b that slides within the outer portion to provide a telescoping link. The link may use a mechanism such as a ball spline to provide the sliding connection between the outer and inner portions of the link. An intermediate gimbal plate 913 supports the ends 962 of the outer portions 916a of the links with a fixed distance between the outer ends thus constraining the inner portions 916b of the links to extend equally from the outer portions. This maintains an equal distance between the first end 960 and second end 964 for each of the three links 916.

Other mechanisms may be used to maintain an equal distance between the first end and second end. For example, a double acting hydraulic piston may be provided in each link. The inboard chamber of one piston may be coupled to the outboard chamber of an adjacent piston to cause all pistons and their associated links to extend and retract in unison. As a further example, a cable and pulley system may be used to cause all links to extend and retract by the same amount. It will be appreciated that a moving counterweight is required to counterbalance a spatial linkage with adjustable length links.

It may be desirable to provide a brake that prevents the outboard gimbal plate from moving relative to the inboard gimbal plate. This may be accomplished by preventing rotation about two of the axes of rotation provided by the pivotal couplings. The two axes may be braked in the same pivotal coupling or in two different pivotal couplings.

Figure 10:
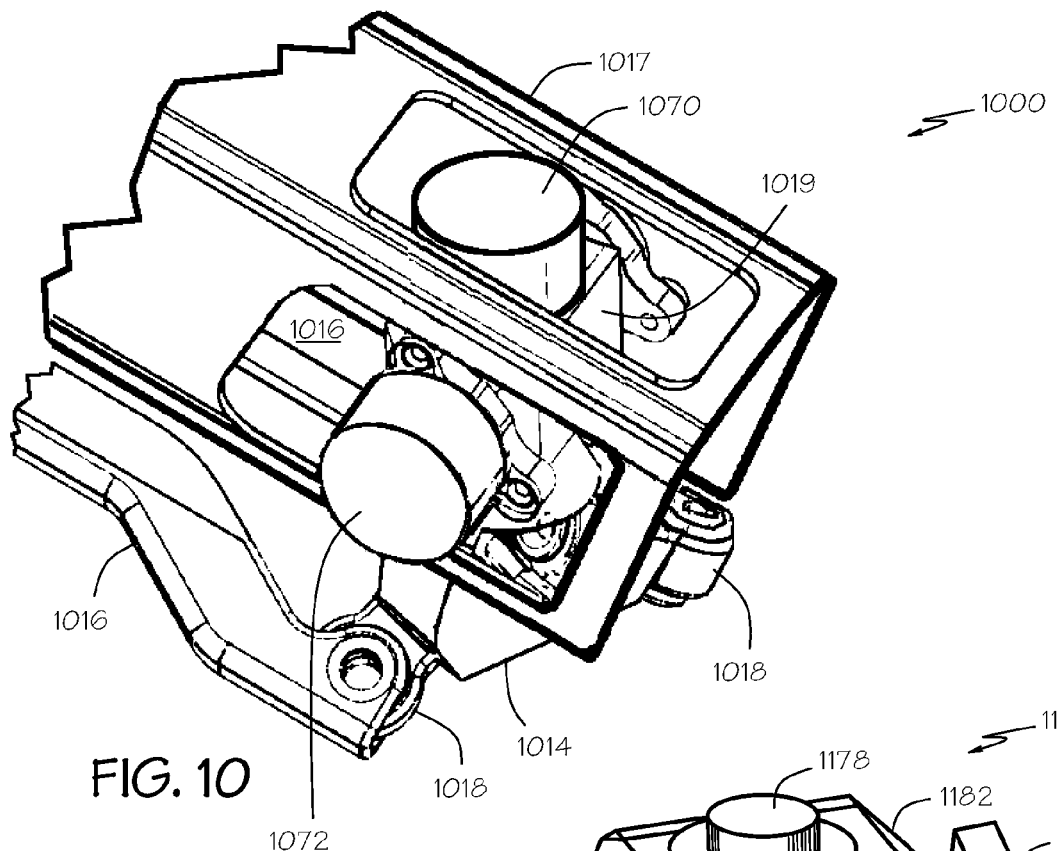
FIG. 10 is a pictorial view of a brake mechanism of another embodiment of the invention.

FIG. 10 shows one end of a spatial linkage 1000 that includes a pivotal coupling 1019 with a brake. It may be seen that the link 1017 coupled to the braked pivotal coupling 1019 is enlarged as compared to the remaining links 1016 coupled to unbraked pivotal couplings 1018. Brake mechanisms 1070, 1072 are provided on each of the rotational axes of the pivotal coupling 1019 to prevent rotation about each axis when the brake mechanism is engaged for that axis. The brake mechanism may be any mechanism that prevents rotation of an axis of the pivotal coupling. The brake may be manually actuated or it may be remotely actuated by means such as, but not limited to, electric, hydraulic, pneumatic, magnetic, or mechanical means.

Figure 11:
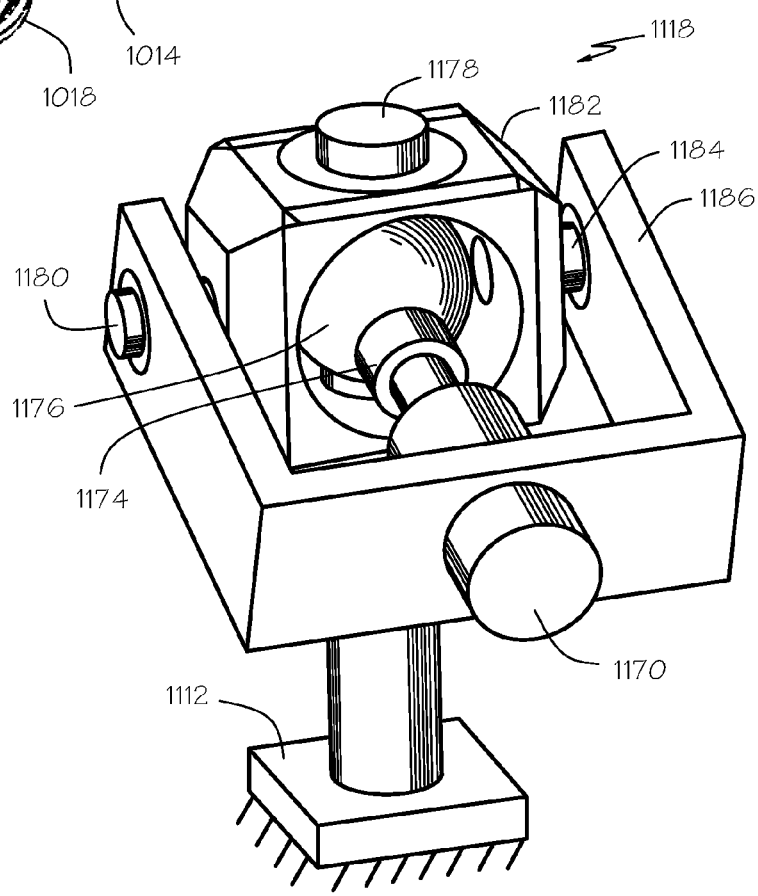
FIG. 11 is a pictorial view of another brake mechanism of another embodiment of the invention.

FIG. 11 shows another pivotal coupling 1118 with a brake. A pivot block 1182 is rotatably supported by a first axle 1178 fixedly coupled to one of the gimbal plates 1112 of the spatial linkage. A yoke 1186 is rotatably supported by a discontinuous second axle 1180, 1184 coupled to the pivot block 1182. The yoke 1186 would be coupled to one of the links of the spatial linkage.

A spherical braking surface 1176 is fixedly coupled to the first axle 1178. Thus the spherical braking surface 1176 is fixed with respect to the gimbal plate 1112. The spherical braking surface may be a portion of a complete spherical surface. The yoke 1186 supports a brake mechanism 1170. The brake mechanism presses a brake pad 1174 against the spherical braking surface 1176 to prevent relative motion between the yoke 1186 and the gimbal plate 1112. When the brake is engaged it prevents the outboard gimbal plate from moving relative to the inboard gimbal plate. The brake may be manually actuated or it may be remotely actuated by means such as, but not limited to, electric, hydraulic, pneumatic, magnetic, or mechanical means.

If a third degree of freedom is provided such as an outboard or inboard sliding support or coupling or extensible links, then it may be desirable to provide a brake that holds the sliding load in a fixed position. The brake on the third degree of freedom may be coupled to the brake that locks the outboard gimbal plate in a fixed position so that a user can lock all degrees freedom with a single action.

The disclosed spatial linkage may be used for supporting a robotic arm to provide freedom of motion for setting a position of the robotic arm. The outboard gimbal plate may rigidly support the robotic arm. The inboard gimbal plate may provide a ground support for the robotic arm. Three or more links of equal length couple the outboard gimbal plate to the inboard gimbal plate. The links are coupled to the gimbal plates with pivotal couplings that allow the outboard gimbal plate to move relative to the inboard gimbal plate and preventing relative rotation between the outboard gimbal plate and the inboard gimbal plate. The supported robotic arm may be positioned with respect to the grounded inboard gimbal plate while remaining in a fixed orientation relative to the inboard gimbal plate.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A spatial linkage comprising:
   an inboard gimbal plate that provides a ground for the spatial linkage;
   an outboard gimbal plate;
   at least three links, each link having a longitudinal axis and two pivotal couplings disposed at opposite ends of the longitudinal axis, each link pivotally coupled to the outboard gimbal plate at a first end of the longitudinal axis and pivotally coupled to the inboard gimbal plate at a second end of the longitudinal axis opposite the first end, the pivotal couplings allowing the outboard gimbal plate to move relative to the inboard gimbal plate with two degrees of freedom and keeping the outboard gimbal plate parallel to the inboard gimbal plate;

a load coupled to the outboard gimbal plate; and a counterweight coupled to at least one of the links on the opposite side of the inboard gimbal plate from the outboard gimbal plate to counterbalance the load regardless of a position of the load with respect to the outboard gimbal plate.

2. The spatial linkage of claim 1 wherein the load is a cantilevered load coupled to the outboard gimbal plate.

3. The spatial linkage of claim 2 wherein the cantilevered load has a movable center of gravity.

4. The spatial linkage of claim 1 further comprising:

a grounded sliding support coupled to the inboard gimbal plate such that the inboard gimbal plate is movable laterally along the length of the sliding support and is constrained in all other lateral directions and rotations.

5. The spatial linkage of claim 4 wherein the sliding support includes a counterbalance that maintains the position of the spatial linkage on the sliding support.

6. The spatial linkage of claim 1 further comprising a brake coupled to at least one pivotal coupling such that the brake can be engaged to prevent the outboard gimbal plate from moving relative to the inboard gimbal plate.

7. The spatial linkage of claim 1 wherein the distance between the first end and the second end of the longitudinal axis of each link is adjustable such that the distance remains equal for each of the links.

8. A setup joint system for a robotic arm, the setup joint system comprising:

an inboard gimbal plate that provides a ground for the setup joint system;

an outboard gimbal plate that supports the robotic arm;

at least three links, each link having a longitudinal axis and two pivotal couplings disposed at opposite ends of the longitudinal axis, each link pivotally coupled to the outboard gimbal plate at a first end of the longitudinal axis and pivotally coupled to the inboard gimbal plate at a second end of the longitudinal axis opposite the first end, the pivotal couplings allowing the outboard gimbal plate to move relative to the inboard gimbal plate and keeping the outboard gimbal plate parallel to the inboard gimbal plate; and a counterweight coupled to at least one of the links on the opposite side of the inboard gimbal plate from the outboard gimbal plate to counterbalance the robotic arm regardless of a position of the robotic arm with respect to the outboard gimbal plate.

9. The setup joint system of claim 8 wherein the outboard gimbal plate supports the robotic arm as a cantilevered load coupled to the outboard gimbal plate.

10. The setup joint system of claim 9 wherein the robotic arm has a movable center of gravity.

11. The setup joint system of claim 8 further comprising:

a grounded sliding support coupled to the inboard gimbal plate such that the inboard gimbal plate is movable laterally along the length of the sliding support and is constrained in all other lateral directions and rotations.

12. The setup joint system of claim 11 wherein the grounded sliding support includes a counterbalance that maintains the position of the spatial linkage on the sliding support.

13. The setup joint system of claim 8 further comprising a brake coupled to at least one pivotal coupling such that the brake can be engaged to prevent the outboard gimbal plate from moving relative to the inboard gimbal plate and hold the robotic arm in a fixed position.

14. The setup joint system of claim 8 wherein the distance between the first end and the second end of the longitudinal axis of each link is adjustable such that the distance remains equal for each of the links.

15. A method of supporting a robotic arm that provides freedom of motion for setting a position of the robotic arm, the method comprising:

supporting the robotic arm with an outboard gimbal plate;

providing a ground support for the robotic arm with an inboard gimbal plate;

coupling the outboard gimbal plate to the inboard gimbal plate with at least three links, each link having a longitudinal axis and two pivotal couplings disposed at opposite ends of the longitudinal axis, each link pivotally coupled to the outboard gimbal plate at a first end of the longitudinal axis and pivotally coupled to the inboard gimbal plate at a second end of the longitudinal axis opposite the first end, the pivotal couplings allowing the outboard gimbal plate to move relative to the inboard gimbal plate and keeping the outboard gimbal plate parallel to the inboard gimbal plate; and substantially balancing the robotic arm by a counterweight coupled to at least one of the links on the opposite side of the inboard gimbal plate from the outboard gimbal plate to counterbalance the robotic arm regardless of a position of the robotic arm with respect to the outboard gimbal plate.

16. The method of claim 15 further comprising supporting the robotic arm as a cantilevered load coupled the outboard gimbal plate.

17. The method of claim 15 further comprising sliding the inboard gimbal plate on a grounded sliding support such that the inboard gimbal plate is movable laterally along the length of the sliding support and is constrained in all other lateral directions and rotations.

18. The method of claim 15 further comprising maintaining the position of the inboard gimbal plate on the sliding support with a counterbalance on the grounded sliding support.

19. The method of claim 15 further comprising engaging a brake coupled to at least one pivotal coupling to prevent the outboard gimbal plate from moving relative to the inboard gimbal plate and hold the robotic arm in a fixed position.

20. The method of claim 15 further comprising adjusting the distance between the first end and the second end of the longitudinal axis of each link such that the distance remains equal for each of the links.

* * * * *